United States Patent [19]

Hause et al.

[11] 4,096,755
[45] Jun. 27, 1978

[54] ULTRASONIC INSPECTION APPARATUS

[75] Inventors: Leroy Robert Hause, Seattle; Clarence William Coplin, Auburn, both of Wash.

[73] Assignee: The Boeing Company, Seattle, Wash.

[21] Appl. No.: 829,400

[22] Filed: Aug. 31, 1977

[51] Int. Cl.$^2$ ............................................ G01N 29/04
[52] U.S. Cl. ...................................... 73/598; 73/618
[58] Field of Search .................... 73/597, 598, 618–626

[56] References Cited

U.S. PATENT DOCUMENTS

| 2,439,130 | 4/1948 | Firestone | 73/598 |
| 3,512,400 | 5/1970 | Lynnworth | 73/598 X |
| 3,555,889 | 1/1971 | Weighart | 73/626 X |
| 3,832,887 | 9/1974 | Zeutshel | 73/598 |

Primary Examiner—James J. Gill
Attorney, Agent, or Firm—Thomas H. Murray

[57] ABSTRACT

Ultrasonic inspection apparatus is described comprising a linear array of contact ultrasonic transducers mounted on a carriage which moves over a surface to be inspected such that a relatively wide path is inspected as the carriage traverses the test surface. The contact transducers arranged in a transmit-receive-transmit mode detect variations in surface sound wave velocity resulting from impact damage to the surface being inspected. When a damaged area exceeding a predetermined area is detected, one of a plurality of indicator lamps associated with the receive transducer is momentarily energized. In addition, when a defect is detected by any one of the receive transducers, a master indicator lamp is energized for a relatively long period of time in order to signal the operator that one of the transducers in the array has sensed a defect. Thus, if the operator has not noticed the momentary energization of one of the lamps associated with a single receive transducer, he will nevertheless notice the master indicator and can then retrace the path of travel of the carriage to precisely locate a defect by observing the separate indicators for each receiving transducer.

8 Claims, 6 Drawing Figures

ULTRASONIC INSPECTION APPARATUS

BACKGROUND OF THE INVENTION

The inspection of newly-manufactured hardware for aircraft and the like can generally be handled by an inspection facility located close to the manufacturing site, with test equipment designed for production compatibility. In the field, however, in-service inspection is most often performed by portable test equipment and hand scanning. This is a slow, tedious operation where large surfaces are concerned. Furthermore, in the case of complex structures, such as bonded aluminum, honeycomb parts with chem-milled skins, stiffeners, access ports and the like, either a hand-scanning technique or some sort of portable small scale scan-record system is required. For large structures with uniform instrument response over large areas, a test technique is required where a wide path can be swept by one or more sensing devices.

One such structure which must be inspected for damage, for example, is an aircraft radome. In such radomes, damage to the composite materials from impacts can eventually lead to primary, catastrophic failure. The most common sources of impact damage are careless handling during routine maintenance, bird strikes, and hailstone damage. Due to the toughness of the external coating of the radome, damage can occur without any visible indication. Established requirements, based on extensive fatigue tests, indicate that any damaged area exceeding one inch in the major dimension must be repaired. Continued in-flight stresses could cause this damaged area to grow until failure occurs, particularly in the edge area or "bull-nose" section.

The present methods of in-service inspection of radomes and other similar aircraft structures for location of impact damage are limited primarily to single probe hand-scanning methods or infrared scanning techniques which require very expensive equipment and are somewhat limited when the ambient temperature reaches lower extremes. Utilizing the hand-scan method, exploration of an entire radome, for example, entails a tedious one or two-shift operation. There is, therefore, a need for a rapid scanning method for testing aircraft radomes and the like which, at the same time, will accurately and precisely locate any defects in the structure.

SUMMARY OF THE INVENTION

In accordance with the present invention, ultrasonic inspection apparatus is provided comprising a carriage movable over a surface to be ultrasonically inspected. Mounted on the carriage are alternate transmitting and receiving ultrasonic transducers arranged in a linear array extending transverse to the direction of movement of the carriage and in contact with the surface to be inspected such that the ultrasonic wave energy from a transmitting transducer will pass through the surface to an adjacent receiving transducer. As each of the transmitting transducers generates a burst of sound in the surface, the sound will travel to and be received by a receiving transducer.

Under normal circumstances, with no defects between an adjacent transmitting and receiving transducer pair, the Lamb wave sound velocity will be at a given value. If, however, a defect exists between an adjacent transmitting and receiving pair, there is a reduction in the Lamb wave velocity of the sound wave which may be detected as a shift in phase in the received wave. Accordingly, means are provided for detecting a phase shift in the sound received by a receiving transducer due to a defect in the surface. The phase shift detecting means may, for example, comprise a zero crossing detector or any other suitable phase shift measuring apparatus.

A separate indicator responsive to received sound is provided for each of the receiving transducers for the purpose of momentarily indicating a shift in phase, indicative of a defect. In view of the fact that this momentary indication may be missed by the operator of the inspection apparatus, a single master indicator is provided for all of the receiving transducers. This single master indicator is actuated for a predetermined period of time longer than the momentary indications of the separate indicators whenever a defect is sensed by any one of the separate detecting devices.

The indicators, for example, may be lamps. As the carriage passes over a surface to be inspected, the presence of a defect between any of the transducers in the linear array will be indicated by the master indicator. When this occurs, the operator can then retrace the path of travel of the carriage to locate precisely the location of the defect by observing the separate indicators for each transducer pair.

The above and other objects and features of the invention will become apparent from the following detailed description taken in connection with the accompanying drawings which form a part of this specification, and in which.

Figure 5:
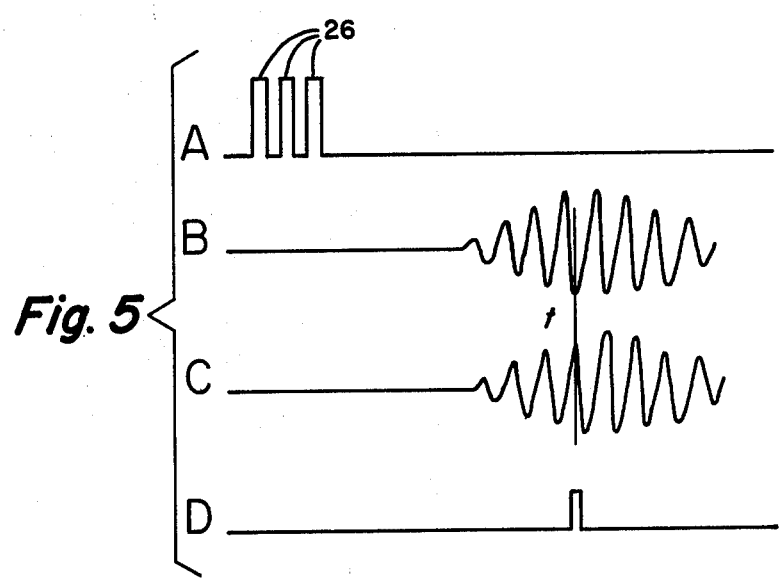
Figure 6:
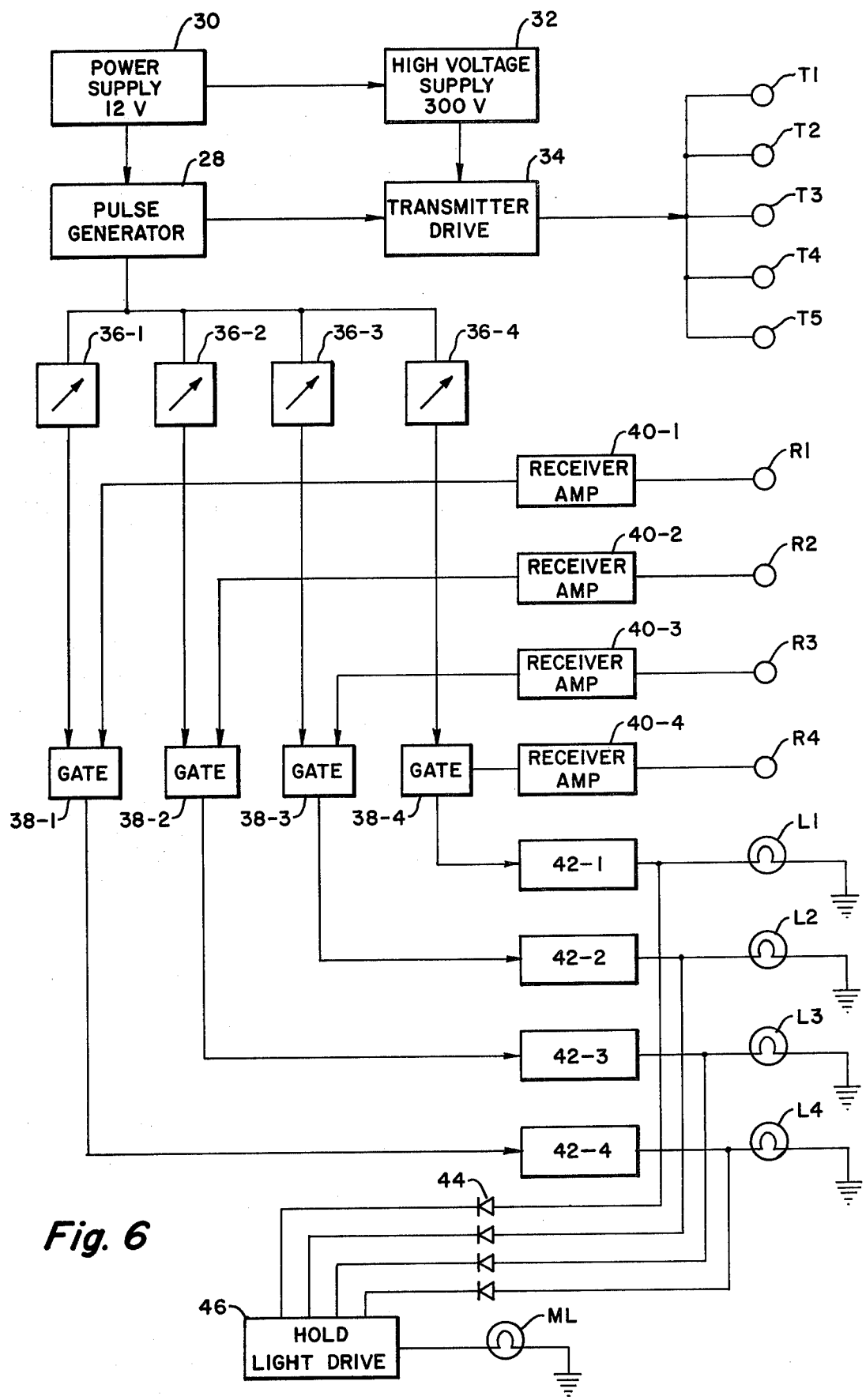

FIG. 5 comprises waveforms illustrating the transmitted ultrasonic signal and the received signal for the case where no damage is present in the surface being inspected and the case where damage is present; and FIG. 6 is a block schematic circuit diagram of the inspection apparatus of the invention.

Figure 1:
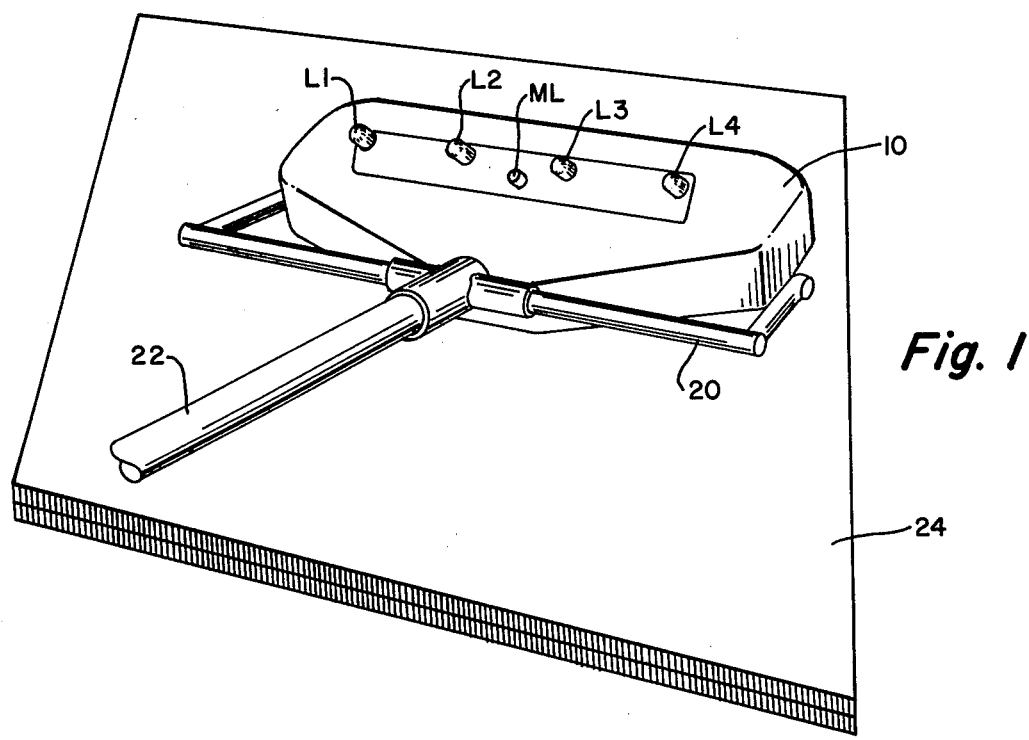
FIG. 1 is a perspective view of the ultrasonic inspection apparatus of the invention showing the manner in which a carriage having ultrasonic transducers thereon may move over a surface to be inspected.
Figure 2:
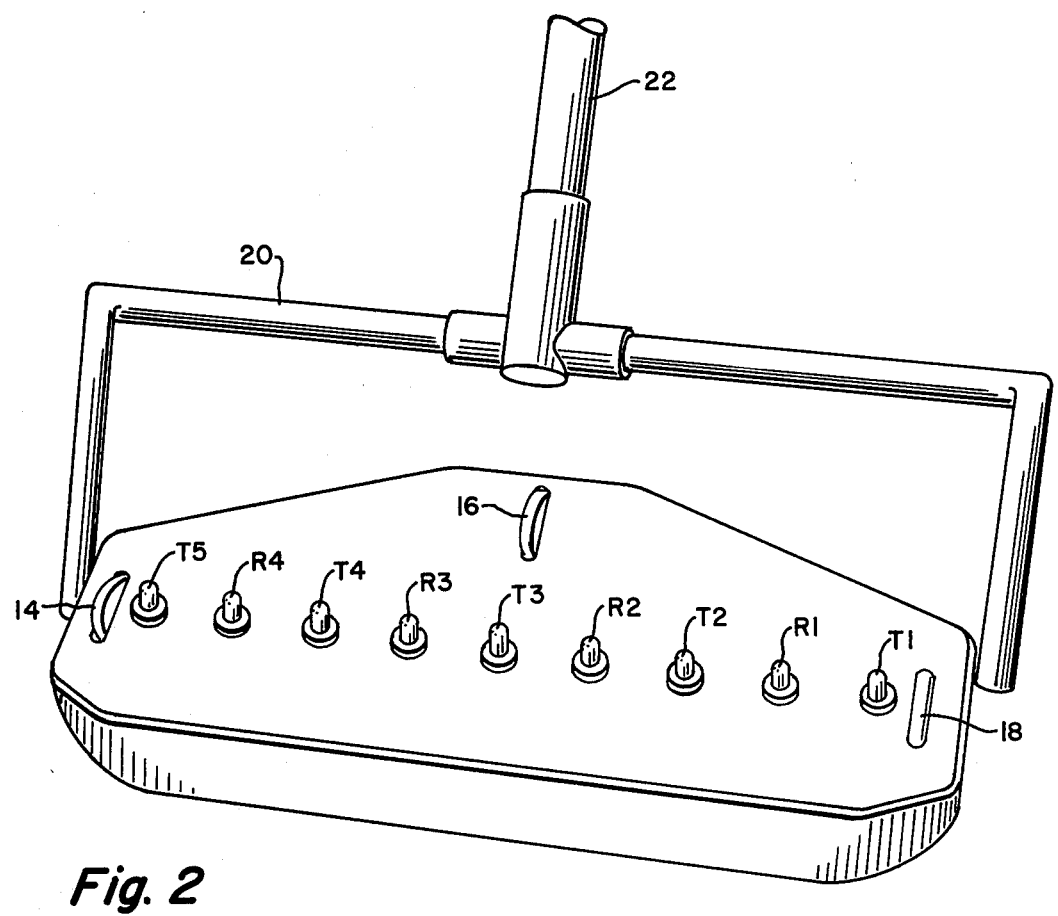
FIG. 2 is a perspective bottom view of the apparatus of FIG. 1.

With reference now to the drawings, and particularly to FIGS. 1 and 2, the inspection apparatus includes a housing 10 having three wheels 14, 16 and 18 projecting through slots in its lower surface. The inspection apparatus is of a "carpet sweeper" configuration and is provided with a yoke 20 connected to an upstanding handle 22 in order that the housing 10 can be pushed or pulled over a surface to be inspected, such as a honeycomb panel 24 in FIG. 1. Projecting through the bottom of the housing 10, as shown in FIG. 2, is a plurality of ultrasonic transducers. There are five transmitting transducers T1-T5 and four receiving transducers R1-R4. As shown, each receiving transducer is interposed between a pair of transmitting transducers.

Figure 3:
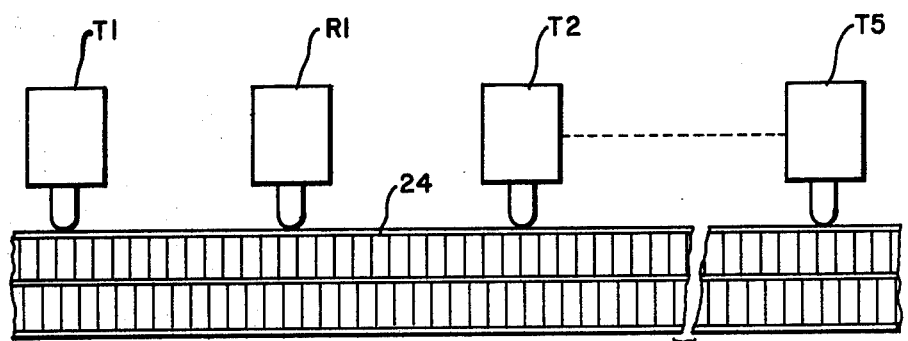
FIG. 3 is a schematic illustration showing the relationship of the transmitting and receiving transducers in the inspection apparatus of the invention.
Figure 4:
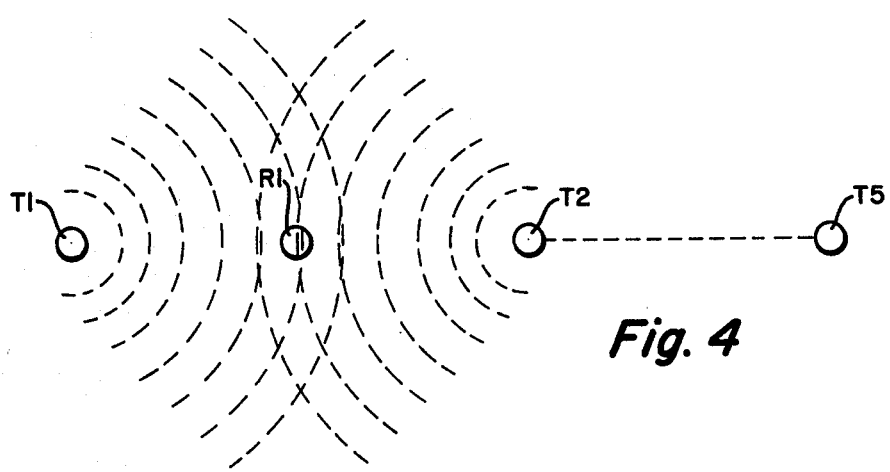
FIG. 4 is a schematic illustration showing the manner in which sound waves travel through a surface being inspected from a transmitting transducer to a receiving transducer.

The interrelationship between the receiving and transmitting transducers is perhaps best shown in FIGS. 3 and 4. Each transducer is a conventional contact piezoelectric transducer which is spring-loaded so as to urge the sensing probe of the transducer into firm contact with the surface 24 being inspected. As best shown in FIG. 4, the sound generated in the test material surface by the transmitter transducers T1 and T2, for example, propagates radially outwardly as a Lamb wave to the receive transducer R1. It will be appreciated, of course, that while only three transducers are shown in FIG. 4, the remaining transmit and receive transducers in the array operate similarly. Furthermore, the sound velocity through the surface being tested is a function of the laminate mass and modulus, or stiffness. Impact damage to the test piece results in either core crazing, ply delamination, or both. The presence of any of these conditions results in a reduction of the stiffness parameter, with an accompanying reduction in Lamb wave velocity. The detection of damaged areas, then, may be accomplished by monitoring for changes in the Lamb wave sound velocity.

In FIG. 5, waveform A illustrates the ultrasonic waveform transmitted by the transmitter T1-T5. It comprises a burst of pulses 26 typically having a frequency of about 25 kilohertz. The burst of pulses 26 recurs at a rate of about 150 bursts per second, only one of such bursts being shown in FIG. 5. Thus, each transmitter transducer T1-T5 generates a burst of sound in the surface 24 which radiates outward from the transmitter as shown in FIG. 4. At some time $t$ after the generation of the sound burst 26, each receive transducer detects the algebraic summation of the sound generated by its neighboring transmitters. Waveform B represents the waveform received by a receive transducer in the absence of any damage to the surface 24. If a sample of the received signal voltage is taken at time $t$, it will be noted that, for the undamaged condition, the voltage will be a minus value. When a damaged area is encountered, however, the sound velocity is reduced with the result that the received signal is delayed as shown by waveform C. Under these circumstances, waveform C has a positive value at time $t$ rather than a negative value as in waveform B where no damage is present. Accordingly, by detecting the shift in phase of the received signal by a zero crossing detector or some other suitable phase detecting means, it is possible to determine whether a defect occurs between a transmitter-receiver pair.

Reverting again to FIG. 1, it will be noted that four lamps L1-L4 project through the upper surface of the housing 10. As will be understood from the following description of the control circuitry for the inspection apparatus, every time a defect is detected by one of the receiving transducers R1-R4, an associated one of the lamps L1-L4 will be energized momentarily. In addition, whenever a defect is sensed by any one of the receiving transducers R1-R4, a master indicator lamp ML will be energized and will remain energized for a period of time, on the order of 1 second or more. Thus, as the inspection apparatus is pushed or pulled over the surface being inspected, one or more of the lamps L1-L4 will be momentarily energized as a transmitter-receiver pair passes over a defect. At the same time, the lamp ML will be energized whenever a defect is sensed by any transmitter-receiver pair.

The control circuitry for the inspection apparatus is shown in FIG. 6. It includes a pulse generator 28 powered by a 12-volt power supply 30. The power supply 30 also powers a high voltage supply 32. The voltage supply 32 may, for example, include a suitable chopper. Output pulses, corresponding to the pulses 26 in waveform A of FIG. 5, are applied through a transmitter drive circuit 34 to all of the transmit transducers T1-T5 in parallel. At the same time, the pulse generator applies a pulse to delay lines 36-1 through 36-4 each of which generates the pulse shown in waveform D of FIG. 5, this pulse occurring at time $t$. Each of the delay lines is separately adjustable to compensate for transducer and/or circuit variations. The pulse from delay lines 36-1 through 36-4 (waveform D) is then applied to each of four gates 38-1, 38-2, 38-3 and 38-4. Also applied to the gates are the outputs of receiver amplifiers 40-1, 40-2, 40-3 and 40-4. These receiver amplifiers are, in turn, connected to each of the receiving transducers and amplify the waveform B or C detected by the receiving transducers.

With the arrangement shown, the gates 38-1 through 38-4 will open at time $t$ shown in FIG. 5 to thereby pass that portion of the received waveform occurring at time $t$ to an associated level detector light drive 42-1, 42-2, 42-3 or 42-4. The circuits 42-1 through 42-4 include, for example, a zero crossing detector which will detect the existence of a positive-going signal. Consequently, if no defect exists between a transmitting and receiving transducer and waveform B of FIG. 5 results, the circuit 42-1, for example, will not be triggered to energize lamp L1. On the other hand, if a defect does exist, the positive-going signal of waveform C in FIG. 5 will be detected and an associated lamp L1-L4 will be energized momentarily.

At the same time, the outputs of the detectors 42-1 through 42-4 are applied through diodes 40 to a hold-and-light drive circuit 46 which, in turn, is adapted to energize the master indicator lamp ML. The arrangement is such that whenever an output occurs from one of the detectors 42-1 through 42-4, the circuit 46 will be triggered to energize the master indicator lamp ML for a period of at least 1 second.

During normal scanning operations, the scan speed can reach 3 or 4 feet per second. At this speed, a small defect in the one-half inch to one-inch diameter range would go unnoticed since the channel lamp L1-L4 could not be able to respond over this short time period. Therefore, the master indicator lamp ML is added which remains energized at least 1 second when any of the four channels momentarily responds to a defect. To eliminate stray noise problems, this momentary signal from one of the detectors 42-1 through 42-4 must exceed approximately 1 millisecond in duration. That is, circuit 46 will not respond to signals below one millisecond in duration. When scanning, therefore, if the operator observes an indication by the master indicator lamp ML, he can reverse the inspection apparatus and slowly traverse the area until the indicating channel indicator L1-L4 becomes energized. The operator now knows the exact location of the defect. Additionally, the operator may move the scanner to permit another channel over the suspected area to verify the presence of a defect.

Although the invention has been shown in connection with a certain specific embodiment, it will be readily apparent to those skilled in the art that various changes in form and arrangement of parts may be made to suit requirements without departing from the spirit and scope of the invention.

We claim as our invention:

1. Ultrasonic inspection apparatus comprising a carriage movable over a surface to be ultrasonically inspected, alternate transmitting and receiving ultrasonic transducers mounted on said carriage in a linear array and in contact with the surface to be inspected such that ultrasonic wave energy from a transmitting transducer will pass through the surface to an adjacent receiving transducer, means for causing each of said transmitting transducers to generate a burst of sound in the surface, a separate detector for each of said receiving transducers for detecting a shift in phase in the sound received by its associated receiving transducer due to a defect in the surface, a separate indicator for each of the receiving transducers for momentarily indicating a shift in phase indicative of a defect, a single master indicator for all of said receiving transducers, and means for actuating said master indicator for a predetermined period of time longer than the momentary indications of the separate indicators whenever a defect is sensed by any of the separate detectors.

2. The apparatus of claim 1 wherein each of said separate detectors comprises a zero crossing detector.

3. The apparatus of claim 1 wherein each of said transducers is spring-loaded to urge it into contact with the surface to be ultrasonically inspected.

4. The apparatus of claim 1 wherein each of said indicators comprises an electrical lamp.

5. The apparatus of claim 1 wherein each of said transmitting transducers is driven by a pulse generator, a delay line connected to said pulse generator, receiving amplifiers connected to each of said receiving transducers, and gate means responsive to the outputs of said receiving amplifiers and said delay line for applying received wave energy from the respective receiving transducers to each of said separate detectors.

6. The apparatus of claim 5 wherein wave energy at the outputs of the respective gate means for each of the receiving transducers is delayed in an equal amount.

7. The apparatus of claim 1 including an energizing circuit for said signal master indicator, and diodes connecting the outputs of each of said separate detectors to said energizing circuit.

8. The apparatus of claim 7 wherein said single master indicator will not respond to signals having a time duration below a predetermined level.

* * * * *